United States Patent

Howell et al.

[11] Patent Number: 5,871,011
[45] Date of Patent: Feb. 16, 1999

[54] APPARATUS FOR DELIVERY OF GAS TO PATIENTS

[75] Inventors: Penelope J. Howell, West Yorkshire; John O'Sullivan; David Gill, both of South Yorkshire, all of United Kingdom

[73] Assignee: Barnsley District General Hospital NHS Trust, Barnsley-Yorkshire, England

[21] Appl. No.: 732,497

[22] PCT Filed: Apr. 28, 1995

[86] PCT No.: PCT/GB95/00973

§ 371 Date: Feb. 18, 1997

§ 102(e) Date: Feb. 18, 1997

[87] PCT Pub. No.: WO95/29724

PCT Pub. Date: Nov. 9, 1995

[30] Foreign Application Priority Data

Apr. 28, 1994 [GB] United Kingdom .................... 9408452

[51] Int. Cl.⁶ .................................................. A61M 16/00
[52] U.S. Cl. .............................. 128/206.22; 128/206.21; 128/206.29; 128/911; 128/204.26
[58] Field of Search .................... 128/204.26, 205.12, 128/205.25, 205.27, 912, 911, 207.12, 207.16, 206.22, 206.29, 201.25, 206.19, 206.21, 201.26, 201.27, 201.28, 200.27, 200.28, 204.18, 205.24, 204.17, 204.24

[56] References Cited

U.S. PATENT DOCUMENTS

| 3,993,059 | 11/1976 | Sjostrand | 128/205.24 |
|---|---|---|---|
| 4,151,843 | 5/1979 | Brekke et al. | 128/204.24 |
| 4,440,164 | 4/1984 | Wesjefelt | 128/205.25 |
| 4,461,292 | 7/1984 | Montalbano | 128/204.17 |
| 4,463,755 | 8/1984 | Suzuki | 128/911 |
| 4,621,634 | 11/1986 | Mowachi et al. | 128/912 |
| 4,794,921 | 1/1989 | Lindkvist | 128/911 |
| 4,829,998 | 5/1989 | Jackson | 124/204.18 |
| 5,392,770 | 2/1995 | Clawsen et al. | 128/912 |

FOREIGN PATENT DOCUMENTS

| 63424 | 4/1955 | France | 128/206.29 |
|---|---|---|---|
| 156627 | 12/1904 | Germany | 128/206.29 |
| 763804 | 12/1956 | United Kingdom | 128/911 |

*Primary Examiner*—John G. Weiss
*Assistant Examiner*—V. Srivastava
*Attorney, Agent, or Firm*—Townsend and Townsend and Crew

[57] ABSTRACT

Apparatus (10) is provided for controlled delivery of gas to a patient. The apparatus is particularly useful for delivery of anaesthetic gases in circumstances where the patient is conscious and able to receive gas upon demand and also where ventilation is poor. The apparatus (10) includes an outlet duct (40) for conveying gas from a gas supply (25) to the patient. A waste gas inlet duct (60) is also provided for receiving gas exhaled by the patient. This is connectable to a suction source (at 35) for scavenging the waste gas. The waste gas inlet duct (60) is arranged so that it can receive gas exhaled by the patient with the outlet duct (via a valve or other diverting means (80)) and around the outlet duct (as guided by shroud (70)).

17 Claims, 3 Drawing Sheets

APPARATUS FOR DELIVERY OF GAS TO PATIENTS

The present invention relates to apparatus for use in delivery of gases to patients. The invention finds particular, but not exclusive, use in relation to delivery of anaesthetic gases.

BACKGROUND OF THE INVENTION

There is increasing concern regarding repeated exposure of medical staff to agents which are potentially harmful to them in the long term. Such agents include anaesthetic gases.

Apparatus exists for controlled supply of anaesthetic gases to a patient. Example apparatus currently available incorporates a face mask. The mask is typically constructed to overlie the patient's face around the mouth and to form a tight seal between the mask and face. Other example apparatus includes a rigid mouthpiece on the outlet of the gas supply tube. Rather than overlying the patient's face as in the previous example, the mouthpiece is retained in the patient's mouth.

Apparatus currently available is capable of supplying gas to a patient on demand, that is only as and when required by the patient. In this respect, the apparatus often includes regulator means which incorporate a valve. In use, as a patient inhales, they apply a negative pressure to the gas supply apparatus. When this happens, a valve in the regulator is opened to permit supply of gas to the patient. In the absence of this negative pressure, the valve is closed and so prevents inadvertent release of gas other than when required by the patient. Likewise, when the patient closes their mouth or exhales, the valve is also closed to cut off the supply of gas. In this way, the gas is supplied to the patient only as and when required by them.

Such systems are particularly useful in cases where the patient is essentially in control of the mouthpiece or mask. This situation typically arises in labour or maternity wards. In those circumstances, so-called "gas and air" (a mixture of equal quantities of nitrous oxide and oxygen) is available for supply to the mother-to-be (or patient).

During labour, the patient is typically given a gas supply apparatus having a mouthpiece or mask, such as described above, and is free to draw from it as and when required. For times when the patient does not require the gas, they may remove the mask or mouthpiece from their face. When this is done, the regulator recognises that there is a lack of demand and the relevant valve is closed to shut off supply of gas to the mask or mouthpiece, as appropriate.

In this way, existing apparatus limits the extent to which anaesthetic gas is leaked into the patient's surroundings. It will be appreciated that gas leaked in this way is exposed to medical staff attending the birth. In the long term, this is likely to be detrimental to the health of the medical staff.

However, additional problems also arise in that, even though it is possible to cut off the supply to the patient, gas is nevertheless exhaled by the patient. Thus, when a patient exhales, this supplies a waste mixture of carbon dioxide and some anaesthetic gas into the surrounding atmosphere. As a result, any medical staff in attendance are also exposed to undesirable amounts of waste anaesthetic gas.

This is a particular problem in labour wards which have inadequate ventilation, which reduces likelihood of the exhaled gas being exhausted from the ward.

In the light of concern for health and safety of employees in the workplace, there is a desire to reduce the extent to which medical staff are exposed to waste anaesthetic gases. Indeed, it is expected that statutory maximum limits will be introduced. For example, a possible maximum limit could be 100 parts/million for nitrous oxide as an 8 hour time weighted average.

SUMMARY OF THE INVENTION

The present invention seeks to alleviate at least some of the aforementioned problems.

Accordingly, in one broad aspect the present invention provides apparatus for controlled delivery of gas to a patient, which apparatus is connectable to a means for supplying gas and a means for withdrawing waste gas, the apparatus comprising an outlet duct for conveying gas from the gas supply to the patient and a waste gas inlet duct capable of receiving gas exhaled by the patient into and around said outlet duct.

Thus the present apparatus is distinguished from many prior systems in that it can be used to scavenge waste gas exhaled by the patient into the outlet duct and gas exhaled and thereby released around the outlet duct. This is a characterising feature of the present invention.

In preferred applications of the present invention, the gas supply is of so-called gas and air, commercially available under the registered trade mark ENTONOX.

Suitably, an outlet duct extends laterally from a gas supply line, typically to provide a mouthpiece for the apparatus. Preferably, the outlet duct includes a mouthpiece which comprises a rigid tube member flattened at its free end so as to be generally elliptical in cross-section.

The inlet duct is connectable to a suction source or other means for withdrawing waste gas from the apparatus. The apparatus conveniently includes a gas supply line and a means for releasably coupling the gas supply line to a gas source and a waste gas exhaust line and means for releasably coupling the exhaust line to a suction source. Generally such coupling means will not be interchangeable to ensure that the apparatus is appropriately linked to the suction source and gas supply. Alternatively, or in addition the coupling means may have some form of indicia to distinguish them.

Preferably, the apparatus includes means for diverting gas exhaled into the outlet duct to the waste gas inlet duct. Passage of the diverted waste gas is assisted by the suction source, as described above. Preferably, the diverting means take the form of a valve, arranged to be openable under the influence of waste gas exhaled by a patient thereby to permit the waste gas to communicate with the waste inlet duct. In this regard the gas is typically supplied to the patient at a pressure which is not sufficient to actuate the diverting means.

Suitably, such a valve includes an opening provided in a wall of a gas supply line and a moveable closure member for closing the opening, which closure member is biased towards a closed position and arranged such that pressure of exhaled waste gas is sufficient to displace the movable closure member from the opening.

Preferably, the waste gas inlet duct is arranged so that, in use, it is presented at a level below that of the valve opening. Suitably, the waste inlet duct is also arranged so that, in use, it is spaced from the patient.

In preferred embodiments, the apparatus incorporates a shroud capable of overlying at least part of a patient's face and to provide a chamber for waste gas exhaled by the patient. Preferably, the chamber accommodates at least the patient's nose. In such preferred embodiments, the shroud takes the form of a mask, adapted to overlie at least the nose and mouth of a patient. Preferably, the shroud is constructed of a generally transparent material. In preferred embodiments, the mask is of a form-sustaining material which has some flexibility. This reduces likelihood of the shroud being damaged, or of it injuring a patient, if the patient were to inadvertently lie on it.

In preferred embodiments, the shroud is arranged such that its perimeter does not closely abut the patient. In particularly preferred embodiments, the outlet duct of the apparatus is arranged to extend beyond the perimeter of the shroud such that, in use, the shroud does not abut the patient.

In another broad aspect, the invention concerns a system for delivering gas to a patient and for withdrawing waste gas and which includes apparatus as described above.

Embodiments of the present invention will now be described further, by way of example, with reference to the accompanying drawings in which:

DETAILED DESCRIPTION OF THE INVENTION

Figure 1:
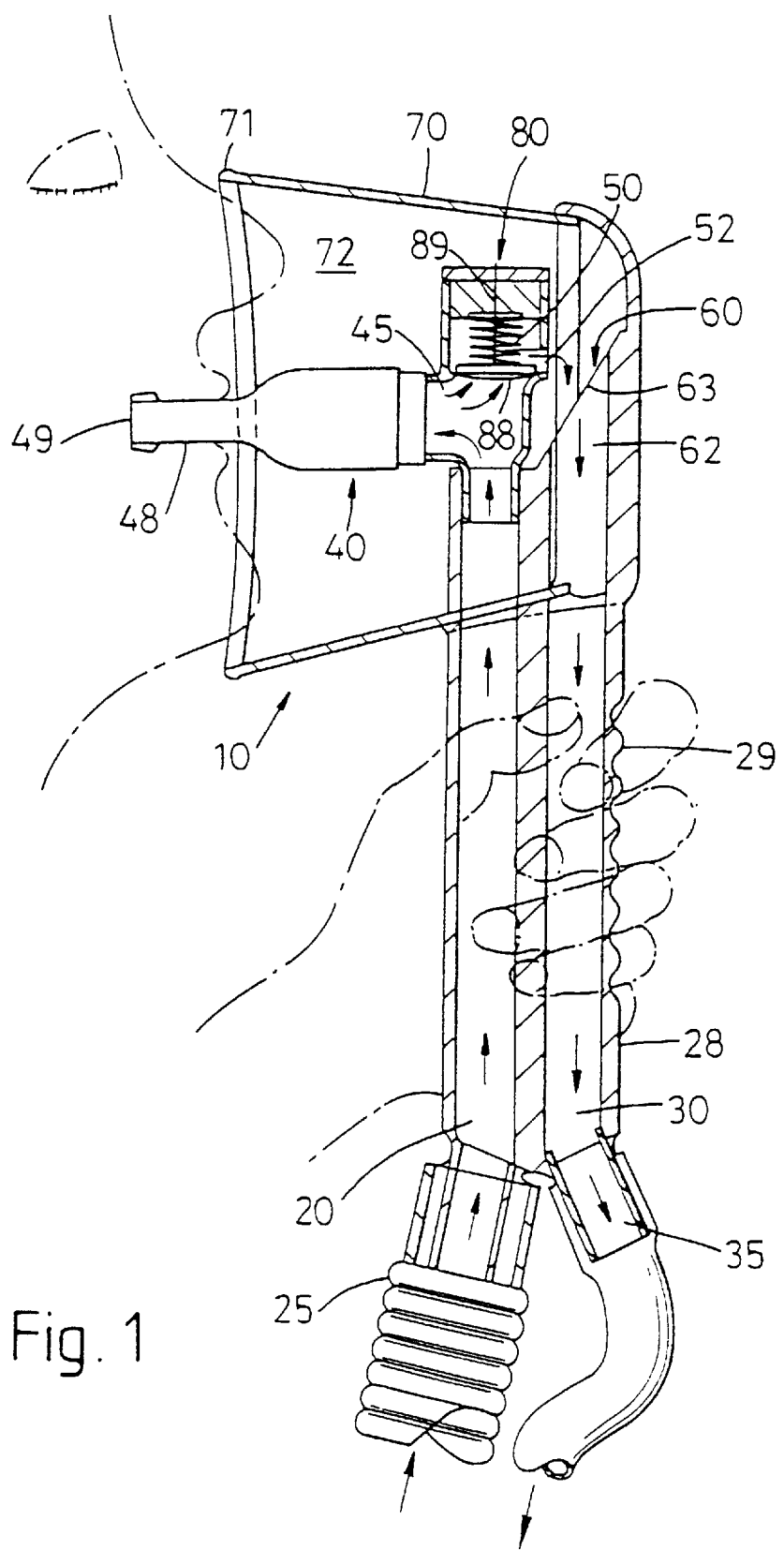
FIG. 1 is a sectional view of example apparatus.
Figure 2:
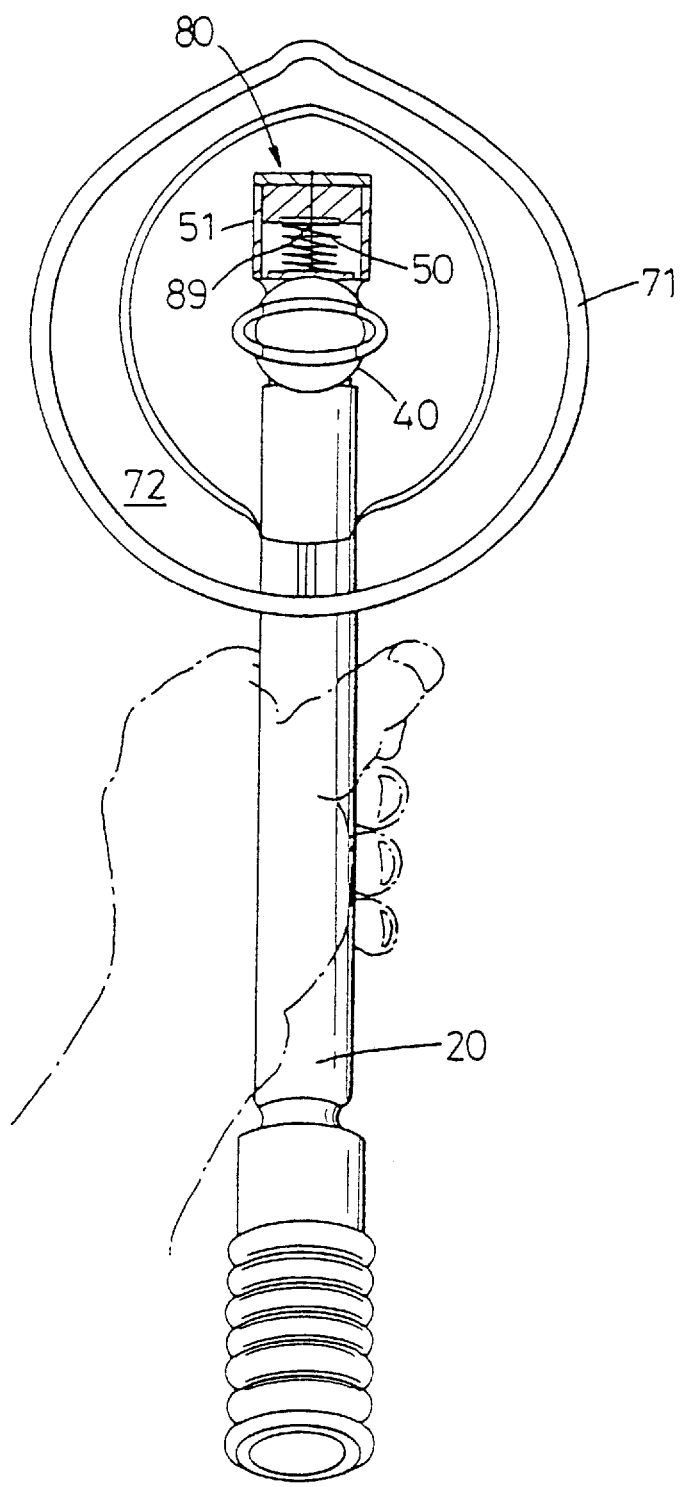
FIG. 2 is a front elevational view of the apparatus of FIG. 1.

The illustrated apparatus 10 includes a gas supply line 20 and a waste gas exhaust line 30. The gas supply line 20 may be coupled to a gas supply (not illustrated) at 25. The waste gas exhaust line 30 may be coupled to a waste gas scavenging system which includes a suction source (not illustrated) at 35. An example of gas which may be delivered using the present apparatus is available under the registered trade mark ENTONOX. As discussed above, this is so-called gas and air. It is a mixture of nitrous oxide and oxygen. Of course, the apparatus may be used for supply of other gases.

The gas supply line 20 and gas exhaust line 30 are accommodated in a casing 28. The casing has surface formations 29 to facilitate grip on the apparatus 10 by the patient.

The apparatus 10 includes an outlet duct 40, inlet duct 60 and shroud 70.

In more detail, the outlet duct 40 comprises a mouthpiece 48 which communicates with the free end of a gas supply line 20 via angled tubing 45. In this way, the mouthpiece 48 extends laterally from the gas supply line 20. The mouthpiece 48 is flattened at its free end 49 and is of an appropriate size and shape so that it may be comfortably accommodated in a patient's mouth. Such mouthpieces are conventional.

The inlet duct 60 comprises a channel 62 having an inclined open end 63.

The angled tubing 45 of the outlet duct 40 includes means for diverting gas from the outlet duct 40 to the waste inlet duct 60. The diverting means are indicated generally at 80. In more detail, the angled tubing 45 includes an opening 88. The opening 88 defines a valve seat. A movable closure member 89 is mounted on the seat 88. The closure member 89 is biased into a closed position by biasing means 50 in the form of a compression spring. The closure member 89 is accommodated in a generally cylindrical housing 51 having an outlet port 52 in communication with opening 88.

The shroud 70 is made of a semi-flexible material, such as a plastic. The shroud is constructed to be generally transparent. The shroud has a generally circular perimeter 71 and may be arranged alongside a patient's face so as to define a chamber 72. This is illustrated in FIG. 1.

The base of the shroud 70 is apertured to permit passage of gas supply line 20 and gas exhaust line 30 therethrough. The shroud 70 is typically mounted on the lines 20, 30 in such a way as to permit slight sliding adjustment of the shroud 70 with respect to the lines so as to define an appropriate spacing between the shroud 70 and the grip formations 29 suitable for the user.

The apparatus 10 is constructed so that the free end 49 of mouthpiece 48 extends beyond the perimeter 71 of the shroud 70.

The apparatus may be employed as follows. The free end 49 of mouthpiece 48 is accommodated in a patient's mouth. As and when a patient inhales and draws on the mouthpiece 48, gas is supplied along the supply line 20 to the mouthpiece 48. The gas is supplied upon demand, using regulator means as described above. As with conventional apparatus, when the patient releases their grip on the mouthpiece 48, or perhaps removes it from their mouth, the supply of gas to line 20 is cut off.

The present apparatus differs from existing apparatus in the way in which it scavenges waste gas exhaled from a patient.

Figure 3:
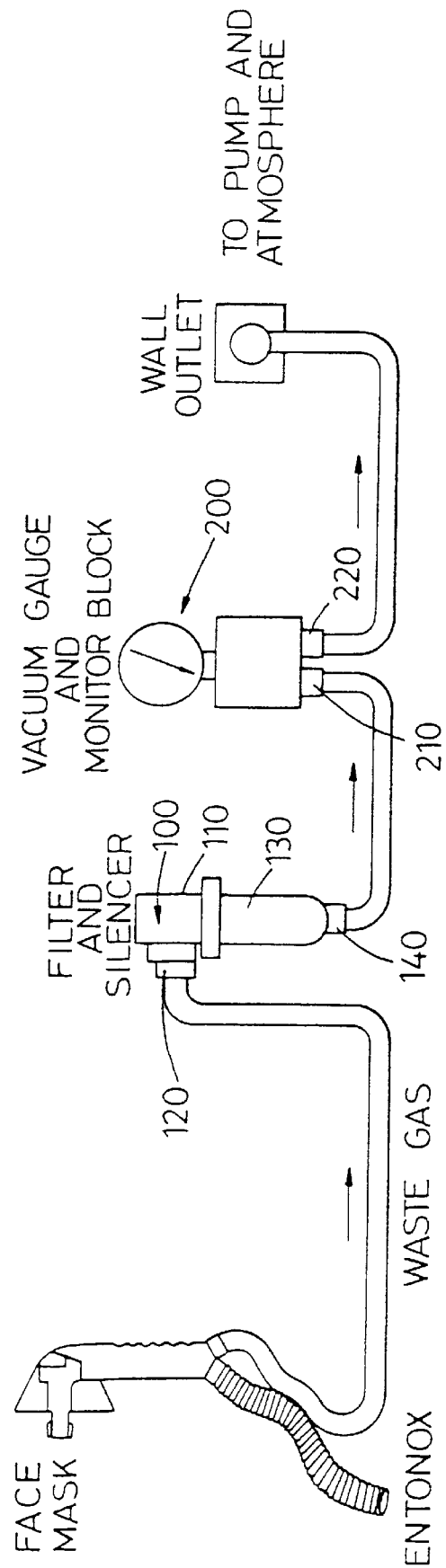
FIG. 3 is a schematic diagram illustrating a waste anaesthetic gas scavenging system which incorporates the apparatus as shown in FIGS. 1 and 2.

In order to scavenge waste gas, a suction source coupled at 35 to the waste gas exhaust line 30 is actuated. When the patient exhales through their nose, waste gas is supplied into chamber 72 defined by shroud 70. The suction source on line 30 draws the waste gas to inlet duct 60. The waste gas is subsequently drawn along line 30. The gas may then be channelled to a remote location for disposal, as illustrated in FIG. 3, for example. Alternatively, the apparatus may be provided with its own dedicated suction source.

When the patient exhales through their mouth, some waste gas will be delivered into chamber 72 around the external periphery of mouthpiece 48. This waste gas may be drawn to waste gas inlet 60 for disposal, in the same way as waste gas exhaled from the nose.

However, when the patient exhales through their mouth rather than their nose, some gas is also delivered into the outlet duct 40. This waste gas will travel to angled tubing 45 and will contact valve seat 88. The pressure of this waste gas is sufficient to displace the moveable closure member 89 from its valve seat 88. This permits the waste gas to escape from opening 88 in the angled tubing 45 and to pass through outlet port 52 in valve housing 51. The waste gas at outlet port 52 is also drawn towards the waste gas inlet 60 by the suction source. The waste gas is thus withdrawn from the locality of the patient for disposal.

As illustrated in FIG. 3, the apparatus 10 may typically be incorporated into a system which includes a filter/silencer unit 100 and a monitor block and vacuum gauge 200. The filter/silencer unit 200 is designed to provide attenuation for the complete apparatus and filtration to prevent any particulate matter or the like from entering the waste gas pipeline system.

The filter/silencer unit 100 conveniently comprises a head block 110 and mounting bracket attached thereto, to enable the unit 100 to be detachably wall mounted. The unit 100 has an inlet port 120 to receive the waste gas line from the apparatus 10. A clear cylindrical filter housing 130 is detachably mounted to the head block 110. The housing 130 incorporates a silencer and filter media (not illustrated).

Example filter media is known in the trade as "Bondina". At the base of filter housing 130, there is an outlet connection 140 to permit passage of gas to the vacuum gauge and monitor block 200.

The vacuum gauge and monitor block 200 is also adapted to be detachably mountable to a wall. The gauge is conveniently scaled from 0 to minus 10 KPA.

The gauge reading is taken to ensure the system is functioning correctly within specified limits. Typically, the system will be functioning with a gauge reading of about 6 KPA Negative.

As shown in FIG. 3, the unit 200 has an inlet port 210 for receiving waste gas from the filter/silencer unit 100. The system will typically supply Entonox (or other gas) at the same flow rate as conventional apparatus. For example the system may suitably scavenge waste gas at a rate which is within a range in the order of about 50 to 180 litres/min or whatever is appropriate to comply with local requirements.

The illustrated apparatus provides advantageous results. It is particularly effective because it is capable of scavenging waste gas exhaled from both the nose and mouth of the patient. The advantages of the present apparatus will be illustrated by the following experimental results.

The following results show sample $N_2O$ exposure levels (ppm) using conventional apparatus which employs as gas supply to a mouthpiece such as used in the present invention

| MIDWIFE | PARTNER | BACKGROUND |
| --- | --- | --- |
| 1488 (419) | 4060 (1142) | 3615 (1017) |
| 997 (398) | — | 1015 (398) |
| 666 (486) | 1854 (1359) | 1707 (1245) |

The figures in brackets denote 8 hour time weighted averages. "Partner" refers to a person attending the birth with the mother-to-be. Experiments under comparable conditions and using apparatus of the present invention have provided exposure levels of as low as from 65(28) to 86(22) for an anaesthetist at respective background levels of from 113 (48) to 185 (46).

Suitably the mouthpiece 48 is releasable from the angled tubing 45 so as to permit it to be disposed of. Typically the angled tubing 45 will also be releasable from the gas supply line 20 so as to permit the shroud 70 to be removed (by sliding it out of engagement with lines 20, 30) for cleaning or for replacement if damaged.

Thus, as shown in FIG. 3 the illustrated apparatus may be coupled to an existing scavenging system for withdrawal of waste gas. In which case the filter/silencer unit, monitor block and vacuum gauge are employed to protect the apparatus from demands made by other users of the scavenging system. Alternatively the apparatus may be provided with its own dedicated suction source for withdrawing exhaled gas. In cases where the apparatus is employed with a dedicated suction source, the filter/silencer unit, monitor block and vacuum gauge described above may be dispensed with.

The present invention has particular application in circumstances where gases are supplied to patients in locations which are poorly ventilated and thus where there is inadequate withdrawal of waste gas. This could be in hospital wards, for example, or in other closed environments such as ambulances. It would, of course, also have application in reasonably well ventilated areas where problems with localised high concentration of gases may arise.

Of course, various modifications may be made to the illustrated embodiment. For example, the valve means or other arrangement included in the diverting means may take various forms. Also, any such valve could be presented in a side wall of a gas supply line, so as to be facing the free end of the mouthpiece, rather than alongside the mouthpiece as illustrated. Also if desired an additional valve could be provided in the gas supply line near its junction with the means for diverting gas exhaled into the outlet duct to the waste gas inlet duct.

We claim:

1. Apparatus for controlled delivery of gas to a patient which apparatus is operatively connectable to a gas supply and to means for withdrawing waste gas, the apparatus comprising an outlet duct for conveying gas from the gas supply to the patient, a chamber disposed around said outlet duct for receiving gas exhausted by said patient, and a waste gas inlet duct having an opening for receiving gas exhaled by said patient from outside of said outlet duct and from inside of said outlet duct; characterized by further including means for diverting exhaled gas from the outlet duct to the waste gas inlet duct, whereby gas exhaled by said patient into said outlet duct is also received in said waste gas inlet duct.

2. Apparatus according to claim 1 which includes a gas supply line and means for releasably coupling the gas supply line to a gas source and a waste gas exhaust line and means for releasably coupling the exhaust line to a suction source.

3. Apparatus according to claim 2 wherein the gas supply outlet duct extends laterally from gas supply line for the apparatus.

4. Apparatus according to claim 1 wherein the gas supply outlet duct includes a releasable mouthpiece for locating in a patient's mouth.

5. Apparatus according to claim 1 wherein the means for diverting exhaled waste gas includes valve means arranged to be openable under the influence of pressure of waste gas exhaled by a patient into the gas supply outlet duct so as to permit the gas supply outlet duct to communicate with the waste gas inlet duct.

6. Apparatus according to claim 5 wherein the valve means includes an opening in a gas supply line, a movable closure member for selectively closing the opening, and means for biasing the member to a closed position, the closure member being arranged to be displaceable once pressure of exhaled gas at the gas supply outlet duct reaches a predetermined level.

7. Apparatus according to claim 1 wherein the waste gas inlet duct is arranged at a level below that of the means for diverting exhaled waste gas from the gas supply outlet duct.

8. Apparatus according to claim 2 wherein the gas supply line and/or the waste gas exhaust line have external surface formations to assist finger grip by a patient.

9. Apparatus according to claim 1 which includes a shroud capable of overlying at least part of a patient's face in use so as to provide the chamber for exhaled waste gas.

10. Apparatus according to claim 9 wherein the shroud is constructed to overlie at least the nose and mouth of a patient.

11. Apparatus according to claim 9 wherein the shroud is at least partly transparent.

12. Apparatus according to claim 9 wherein the waste gas inlet duct is located within the chamber defined by the shroud and the gas supply outlet duct extends outside of the chamber and beyond the perimeter of the shroud.

13. Apparatus according to claim 9 wherein the shroud is mounted in the apparatus so as to permit adjustment of its position relative to the gas supply outlet duct.

14. Apparatus according to claim 9 wherein the shroud is releasable for maintenance.

15. Apparatus according to claim 1 further comprising a gas supply.

16. Apparatus according to claim 1 further comprising a means for withdrawing waste gas exhaled by the patient.

17. Apparatus for controlled delivery of gas to a patient which apparatus is operatively connectable to a gas supply and to means for withdrawing waste gas, the apparatus comprising:

an outlet duct for conveying gas from the gas supply to the patient;

a shroud defining a chamber disposed around said outlet duct for receiving gas exhausted by the patient, the shroud being adapted to be placed over the patient's nose and mouth;

a waste gas inlet duct which is arranged to receive gas that is exhaled by the patient into said chamber directly from the chamber such that the gas exhaled into the chamber by-passes the outlet duct; and means for diverting exhaled gas from the outlet duct and to the waste gas inlet duct such that gas which is exhaled by the patient directly into the outlet duct is received in said waste gas inlet duct through the diverting means.

* * * * *